(12) United States Patent
Kimura et al.

(10) Patent No.: US 7,642,230 B2
(45) Date of Patent: Jan. 5, 2010

(54) ZINC-CONTAINING SUSTAINED-RELEASE COMPOSITION, ITS PREPARATION, AND METHOD FOR PRODUCING THE SAME

(75) Inventors: Michio Kimura, Chigasaki (JP); Tomoko Eto, Yokohama (JP); Yutaka Mizushima, Tokyo (JP)

(73) Assignee: LTT Bio-Pharma Co., Ltd., Tokyo (JP)

( * ) Notice: Subject to any disclaimer, the term of this patent is extended or adjusted under 35 U.S.C. 154(b) by 229 days.

(21) Appl. No.: 10/555,191

(22) PCT Filed: Apr. 1, 2004

(86) PCT No.: PCT/JP2004/004791

§ 371 (c)(1),
(2), (4) Date: Nov. 1, 2005

(87) PCT Pub. No.: WO2004/096179

PCT Pub. Date: Nov. 11, 2004

(65) Prior Publication Data

US 2006/0210629 A1 Sep. 21, 2006

(30) Foreign Application Priority Data

May 1, 2003 (JP) ............................. 2003-126503

(51) Int. Cl.
*A61K 38/02* (2006.01)
*A61K 33/30* (2006.01)
*A61K 33/42* (2006.01)

(52) U.S. Cl. ............................. 514/2; 514/7; 424/400; 424/686; 424/641; 424/601

(58) Field of Classification Search .................... 514/2, 514/7; 424/490, 499, 400, 686, 641, 601
See application file for complete search history.

(56) References Cited

U.S. PATENT DOCUMENTS

| | | | |
|---|---|---|---|
| 6,051,259 A * | 4/2000 | Johnson et al. | 424/502 |
| 6,197,350 B1 | 3/2001 | Yamagata et al. | |
| 6,998,137 B2 * | 2/2006 | Shih et al. | 424/426 |
| 2002/0015737 A1 * | 2/2002 | Shih et al. | 424/499 |
| 2003/0203040 A1 * | 10/2003 | Cleland et al. | 424/490 |

FOREIGN PATENT DOCUMENTS

| | | |
|---|---|---|
| EP | 1002529 A1 | 5/2000 |
| JP | 2002-348234 | 12/2002 |
| JP | 2003-081865 | 3/2003 |
| WO | 03/000282 A1 | 1/2003 |

* cited by examiner

*Primary Examiner*—David Lukton
(74) *Attorney, Agent, or Firm*—Ostrager Chong Flaherty & Broitman P.C.

(57) ABSTRACT

With a simple and high-yield production method, a zinc-containing sustained-release composition capable of stabilizing a physiologically active protein or peptide, typically G-CSF by precipitation and retaining drug efficacy for several days in a living body owing to its sustained releasability is provided. Concretely, a zinc-containing sustained-release composition produced by forming a precipitate by mixing a physiologically active protein or peptide, a water-soluble zinc salt, a water-soluble carbonate and/or a water soluble phosphate aqueous solution. The zinc-containing sustained-release composition may be administered as a zinc-containing sustained preparation by adding a pharmaceutically acceptable additive as is necessary.

14 Claims, No Drawings

ZINC-CONTAINING SUSTAINED-RELEASE COMPOSITION, ITS PREPARATION, AND METHOD FOR PRODUCING THE SAME

The present application is the U.S. national phase application corresponding to and claiming the priority of International Application PCT No. PCT/JP2004/004791, filed Apr. 1, 2004, which claims priority to Japanese Application No. JP 2003-126503, filed May 1, 2003; both applications are hereby incorporated by reference.

TECHNICAL FIELD

The present invention relates to a zinc-containing sustained-release composition, its preparation and a method for producing the same, comprising the step of mixing a protein or peptide having physiological activity and a water-soluble zinc salt with an aqueous solution of a water-soluble carbonate and/or a water-soluble phosphate, thereby forming a precipitate.

BACKGROUND ART

At present, preparations comprising granulocyte colony-stimulating factor (G-CSF) are used against disorders and clinical conditions accompanied by reduction of neutrophils. These preparations may be administered by intravenous injection, subcutaneous injection, or drip infusion, but they should be administered everyday at once or twice time per a day.

This attributes to the poor stability of G-CSF in blood and short half-life, as well as to the requirement that G-CSF should exist at more than a certain concentration in the blood for keeping its drug efficacy. For this reason, a patient is burdened with everyday administration, and hence burdened with excess use of G-CSF. Therefore, preparation that makes it possible to keep the blood level of G-CSF constant is required.

In view of the fact that granulocyte colony-stimulating factor (G-CSF) forms a precipitate with metal ions such as calcium ion and zinc ion, one conventional art attempted to develop a sustained-release preparation based on such a water-insoluble precipitate. For example, a precipitate formed exclusively of a protein and a multivalent metal ion is easy to dissolve, so that desired sustained releasability cannot be achieved as it is. To cope with this, a method in which a second precipitable substance is added to the precipitate composition formed of G-CSF and metal ion for suppressing dissolution of the precipitate formed of G-CSF and metal ion has been proposed (Japanese Patent Laid-Open Publication No. 2003-81865). In this case, the second precipitable substance to be added is, for example, proteins that can bind with a metal ion but have almost no drug efficacy by themselves, such as human serum albumin and the like. It is also disclosed that by adding an acidic mucopolysaccharide such as chondroitin sulfate, the mixed protein can precipitate more efficiently, and the resultant precipitate shows much better sustained releasability of G-CSF.

The above method, however, entails the problem that although 95% or more of G-CSF precipitates by coprecipitation with these proteins when used at a concentration of around several hundred μg/ml, the precipitation efficiency decreases to 90% or lower when the concentration of G-CSF is 1 mg/ml or more. Additionally, since human serum albumin or chondroitin sulfate used as a coprecipitate is a biological material, there arises a safety problem. Also the above method should counter the problem that the use of the biological materials that are necessarily added is refrained because they are expensive and give not a little influence on the production cost. Furthermore, considering the number of process steps depending on the type of composition, there is still room for improvement.

International Publication Number WO 03/000282 discloses combining a growth hormone, sodium hydrogen carbonate, and zinc acetate for the purpose of solidifying the growth hormone (see Examples 1 and 2), and however, it lacks reference to sustained release effect of the formed solid growth hormone. Also, this differs from the composition found by the present inventors for achieving sustained releasability.

Therefore, it is an object of the present invention to provide a water-insoluble preparation which can be prepared more easily than using the aforementioned methods and capable of precipitating a physiologically active protein or peptide such as G-CSF with high yield and stabilizing the same, and enabling the physiologically active protein or peptide to retain its drug efficacy for several days in a living body owing to the sustained-release effect of the obtained precipitate.

In order to achieve this object, the present inventors examined a method that utilizes co-precipitation with a water-insoluble salt of zinc for finding out a substance which is able to make a physiologically active protein having interaction with a zinc ion precipitate with high efficiency in the presence of a zinc ion without using a biological material such as human serum albumin or chondroitin sulfate as descried above.

As a result, it was found that a physiologically active protein having interaction with a zinc ion is contained efficiently in a precipitate formed by mixing a water-soluble zinc salt such as zinc chloride or zinc acetate with a water-soluble carbonate such as sodium hydrogen carbonate or sodium carbonate and/or a water-soluble phosphate such as sodium phosphate.

In brief, the present inventors found that if a zinc binding physiologically active protein such as G-CSF coexists during formation of a precipitate by mixing a water-soluble zinc salt and an aqueous solution of water-soluble carbonate and/or water-soluble phosphate, a precipitate efficiently containing such a physiologically active protein can be formed. Also it was confirmed that the precipitate composition thus obtained could release the physiologically active protein contained therein in a sustained manner.

Also it was found that by using combination of water-soluble carbonate and water-soluble phosphate and varying the mixing ratio thereof, it is possible to control the sustained-release rate of the physiologically active protein such as G-CSF.

As a particulate sustained-release preparation using a similar water-insoluble inorganic salt, a calcium carbonate preparation disclosed in Japanese Patent Laid-open Publication No. 2002-348234 is known. In this case, it is required to form calcium carbonate particulates at a concentration of 1 M or more for making the resultant precipitate contain G-CSF of about 100 μg/ml. Furthermore, since release amount of G-CSF from the resultant precipitate is very small, and therefore, the characteristic of the precipitate is different from that of the precipitate composition of the present invention.

For example, according to the present invention, almost all G-CSF of approximately 1 mg/ml of G-CSF in concentration can be incorporated in the resultant precipitate by simultaneously mixing approximately 20 mM zinc acetate or zinc chloride (zinc concentration: approximately 1.3 mg/ml) and approximately 20 mM sodium hydrogen carbonate and/or a phosphate.

That is, the present inventors found that almost 100% of G-CSF can be precipitated, for example, with zinc of nearly equivalent weight to G-CSF by using a water-soluble zinc salt and a water-soluble carbonate and/or phosphate, and achieved the present invention.

The obtained precipitate is fine enough to pass through an injection needle, so that it can be used as an injectable preparation.

Furthermore, experiment studies using mice have demonstrated that the present invention improves not only yield of precipitate formation of a physiologically active protein but also sustained-release effect in a living body, and the present invention was accomplished.

DISCLOSURE OF THE INVENTION

Therefore, one aspect of the present invention provides a zinc-containing sustained-release composition comprising a precipitate containing a physiologically active protein or peptide obtained by mixing a physiologically active protein or peptide, a water-soluble zinc salt, and an aqueous solution of a water-soluble carbonate and/or a water-soluble phosphate.

More specifically, the present invention is a zinc-containing sustained-release composition wherein the water-soluble zinc salt is zinc acetate or zinc chloride.

Specifically, the present invention provides a zinc-containing sustained-release composition wherein the water-soluble carbonate is sodium carbonate or sodium hydrogen carbonate, and the water-soluble phosphate is sodium phosphate or sodium hydrogen phosphate.

In this case, the water-soluble carbonate improves formation of the precipitation and initial sustained releasability from the precipitate, and the water-insoluble phosphate improves the durability of sustained release of the physiologically active protein or peptide from the precipitate.

More specifically, the present invention provides a zinc-containing sustained-release composition wherein the physiologically active protein is G-CSF, antibody, growth hormone, IFN, EPO, GM-CSF, BDNF, NT-3, interleukin, or FGF.

In more preferred specific aspect, the present invention is a zinc-containing sustained-release composition wherein the zinc-containing sustained-release composition is freeze-dried and in a form suited for subcutaneous injection or intramuscular injection.

In another aspect, the present invention provides a zinc-containing sustained-release preparation comprising the aforementioned zinc-containing sustained-release composition, and more specifically, a zinc-containing sustained-release preparation prepared by adding a pharmaceutically acceptable additive to the aforementioned zinc-containing sustained-release composition, if necessary.

Specifically, the present invention is a zinc-containing sustained-release preparation wherein the pharmaceutically acceptable additive is a dispersant, a surfactant, an antiseptic agent or a stabilizer, and more specifically a zinc-containing sustained-release preparation wherein the pharmaceutically acceptable additive is saccharide.

Preferably, the present invention is a zinc-containing sustained-release preparation wherein it is freeze-dried and is in a form suited for subcutaneous injection and intramuscular injection.

Among others, the present invention is, in particular, a leukocyte increasing agent comprising a zinc-containing sustained-release preparation wherein the physiologically active protein is G-CSF.

In still another aspect, the present invention provides a method for producing a zinc-containing sustained-release composition comprising the step of mixing a physiologically active protein or peptide, a water-soluble zinc salt, and an aqueous solution of a water-soluble carbonate and/or a water soluble phosphate, thereby forming a precipitate containing the physiologically active protein or peptide.

BEST MODE FOR CARRYING OUT THE INVENTION

As described above, one aspect of the present invention provides a zinc-containing sustained-release composition comprising a precipitate containing a physiologically active protein or peptide, which typical compound is G-CSF, obtained by mixing a physiologically active protein or peptide, a water-soluble zinc salt, and an aqueous solution of a water-soluble carbonate and/or a water-soluble phosphate.

The present invention is characterized by forming a precipitate in a pH range from 4.5 to 9.0, in particular. That is, since the pH range is set around neutrality, production without losing activity is possible for a protein such as G-CSF whose activity will be lost at extreme pH values. Furthermore, the present invention is characterized by making G-CSF contained in the precipitate at high ratio. Under the optimum condition of this case, a content of G-CSF not less than 99% is realized.

A water-insoluble sustained-release composition which is a precipitate provided by the present invention is preferably formed by first mixing basically 10 to 2000 μg/ml of G-CSF with a solution of sodium hydrogen carbonate of final concentration of not less than 20 mM, and then adding a solution of zinc acetate or zinc chloride of final concentration of not less than 20 mM, thereby forming a precipitate which is the precipitate sustained-release composition. In this case, preferably, the water-soluble zinc salt is added so that the molar ratio of the physiologically active protein or peptide and zinc in the water-soluble zinc salt is 1:100 or more.

Likewise, as for an antibody, interferon, or growth hormone, it was possible to produce a precipitate composition, which seems to have almost the same properties as those of G-CSF, by the production method of precipitate according to the present invention.

Furthermore, a sustained-release composition which is an objective of the present invention can also be produced by using a phosphate of around neutrality in place of a carbonate although the content of G-CSF in the precipitate decreases more or less. Furthermore, it was also found that by using both a water-soluble carbonate and a water-soluble phosphate and changing the mixing ratio thereof, it is possible to control the sustained-release rate of G-CSF.

Furthermore, by adding an acidic mucopolysaccharide such as chondroitin sulfate or poly(lactic-co-glycolic acid) (PLGA), it is possible to control the sustained-release effect.

In the precipitate composition of the present invention, saccharides such as mannitol and trehalose may be added to the suspension after formation of the precipitate, which is then freeze-dried and re-suspended in injectable distilled water before use.

HPLC analysis was conducted for the precipitates before and after freeze-drying dissolved with EDTA, to find that the elution patterns were not different from that of G-CSF used for forming the precipitates, and that G-CSF did not aggregate or decompose during formation of precipitate or during freeze-drying. Thus, excellent stability of the precipitate was confirmed. It was also confirmed that with a preparation containing the precipitate according to the invention, G-CSF does not get denatured over a month at 37° C. in a storage stability test.

The preparation containing a precipitate composition which is another aspect provided by the present invention, for example, a G-CSF-containing preparation comprises a precipitate obtained by formation of precipitate as described above, and a pharmaceutically acceptable additive such as a dispersant, a surfactant, an antiseptic agent, a stabilizer, or saccharide, and this preparation may be administered by subcutaneous injection, intramuscular injection or the like means.

The preparation of the present invention thus provided, for example, a G-CSF preparation not only keeps its drug efficacy for a week or more by single dose in mice but also reduces the dosage amount compared to the amount of G-CSF which is given everyday for keeping the drug efficacy.

Therefore, the zinc-containing sustained-release composition provided by the present invention is concretely produced by mixing a physiologically active protein or peptide, a water-soluble zinc salt, and an aqueous solution of a water-soluble carbonate and/or a water soluble phosphate, thereby forming a precipitate containing the physiologically active protein or peptide.

In the zinc-containing sustained-release preparation produced by this method, physiologically active proteins or peptides capable of forming a precipitate with a zinc ion can be contained as well as G-CSF. Examples of such physiologically active proteins or peptides include hirudin, interleukin-2 (IL-2), interferon (IFN), etanercept, antibody, TNF antibody, erythropoietin (EPO), granulocyte-macrophage colony stimulating factor (GM-CSF), growth hormone, BDNF, NT-3, FGF, proteins having y-carboxyglutamic acid, recombinant protein preparations with His-tag and the like. Among these, biological factors exhibiting the drug efficacy by small amount are particularly preferred.

For example, when an antibody, interferon, or growth hormone is precipitated in accordance with the method of the present invention, it was contained in the precipitate with a yield as high as that observed in G-CSF, so that comparative sustained-release effect can be expected.

The sustained-release composition provided by the present invention can be prepared into a preparation for parenteral administration by taking advantage of its property.

Examples of the parenteral preparation include injectable preparations (subcutaneous injection, intramuscular injection, intravenous injection, etc.), solution preparations such as drip infusion, nasal preparations such as spray preparation, and preparations for transmucosal administration. Any of these preparations can be prepared in conformance with the method described in "General Rules for Preparations" in The Japanese Pharmacopoeia. In preparation, a carrier, a plasticizer, an isotonizing agent, a stabilizer, and the like that are commonly used in the pharmaceutical field may be appropriately selected and used.

The content of the precipitate composition which is an active ingredient in the sustained-release preparation provided by the present invention cannot be particularly limited. In general, a dosage amount that allows the physiologically active protein or peptide to exert its pharmacological activity and express the effect should be contained in the precipitate composition although it varies depending on the age, gender, body weight, the clinical condition and the like of the patient to be administrated.

EXAMPLES

The present invention will be described in detail by way of examples, however, the present invention is not limited to these examples.

Example 1

Preparation of Precipitate Sustained-Release Composition by Mixing G-CSF with Zinc Acetate or Zinc Chloride (20 mM) and Sodium Hydrogen Carbonate Solution (20 mM), Precipitation Rate of G-CSF, and Comparison with Case Where Calcium was Used as Metal Salt First 50 µl of G-CSF solution (4.0 mg/ml) dissolved in approximately 30 mM phosphate buffer, 8 µl of sodium hydrogen carbonate (0.5 M) and 134 µl of Milli-Q water were mixed, and then the mixture was added with 8 µl of zinc acetate solution (0.5 M) or zinc chloride (0.5 M) under stirring and left at room temperature for 10 minutes. In the same manner, first 50 µl of G-CSF solution (4.0 mg/ml) dissolved in approximately 30 mM phosphate buffer, 8 µl of sodium hydrogen carbonate (0.5 M) and 134 µl of Milli-Q water were mixed, and then the mixture was added with 8 µl of calcium chloride (0.5 M) under stirring and left at room temperature for 10 minutes. These suspensions were centrifuged at approximately 10,000×g. The supernatants were collected and the precipitates were dissolved in 0.1 M EDTA solution (pH 7.4), and the contents of G-CSF contained in the supernatants and precipitates were determined by ELISA method.

The results are shown in Table 1.

TABLE 1

Precipitation rate of G-CSF in precipitate formation by mixing G-CSF with zinc acetate or zinc chloride solution and sodium hydrogen carbonate solution, and precipitation rate of G-CSF by mixing with calcium chloride solution and sodium hydrogen carbonate solution.

| | Content of C-CSF (%) | |
|---|---|---|
| | Supernatant | Precipitate |
| Sodium hydrogen carbonate + Zinc acetate | 0.8 | 99.2 |
| Sodium hydrogen carbonate + Zinc chloride | 0.1 | 99.9 |
| Sodium hydrogen carbonate + Calcium chloride | 93.2 | 6.8 |

As shown in Table 1, at the G-CSF concentration of 1 mg/ml, not more than 10% of G-CSF was contained in the precipitate when the precipitate was formed using calcium chloride. To the contrary, when the precipitate was formed using 20 mM of zinc acetate or zinc chloride, G-CSF was contained in the precipitate with high efficiency of not less than 99%.

In Japanese Patent Laid-open Publication 2002-348234 previously referred to as a conventional art, in order to make G-CSF contained in the precipitate with high efficiency, the precipitate is produced by further adding 2.5 ml of sodium carbonate (1 M) to 650 µl of calcium chloride (5 M) and 250 µl of G-CSF (0.5 mg/ml).

Example 2

Studies of Zinc Concentration Required for Making Precipitate at 99% or More from 1 mg/ml of G-CSF Solution (1) A preparation in which final concentration of zinc is 20 mM was prepared by first mixing 50 μl of G-CSF solution (4.0 mg/ml) dissolved in approximately 30 mM phosphate buffer, 40 μl of sodium hydrogen carbonate (0.1 M) and 70 μl of Milli-Q water, then adding to this solution 40 μl of zinc acetate solution (0.1 M) under stirring, and leaving the resultant solution at room temperature for 10 minutes.

(2) A preparation in which final concentration of zinc is 10 mM was prepared by first mixing 50 μl of G-CSF solution (4.0 mg/ml) dissolved in approximately 30 mM phosphate buffer, 20 μl of sodium hydrogen carbonate (0.1 M) and 110 μl of Milli-Q water, then adding to this solution 20 μl of zinc acetate solution (0.1 M) under stirring, and leaving the resultant solution at room temperature for 10 minutes.

(3) A preparation in which final concentration of zinc is 5 mM was prepared by first mixing 50 μl of G-CSF solution (4.0 mg/ml) dissolved in approximately 30 mM phosphate buffer, 10 μl of sodium hydrogen carbonate (0.1 M) and 130 μl of Milli-Q water, then adding to this solution 10 μl of zinc acetate solution (0.1 M) under stirring, and leaving the resultant solution at room temperature for 10 minutes.

(4) A preparation in which final concentration of zinc is 2 mM was prepared by first mixing 50 μl of G-CSF solution (4.0 mg/ml) dissolved in approximately 30 mM phosphate buffer, 4 μl of sodium hydrogen carbonate (0.1 M) and 142 μl of Milli-Q water, then adding to this solution 4 μl of zinc acetate solution (0.1 M) under stirring, and leaving the resultant solution at room temperature for 10 minutes.

These suspensions (1) to (4) were centrifuged at approximately 10,000×g. The supernatants were collected and the precipitates were dissolved in 0.1 M EDTA solution (pH 7.4), and the amounts of G-CSF contained in the supernatants and precipitates were determined by ELISA method.

The results are shown in Table 2.

TABLE 2

Zinc concentration and G-CSF content of precipitates formed by using zinc acetate and sodium hydrogen carbonate from the solution of 1 mg/ml G-CSF concentration

| Zinc concentration (mM) | Content of G-CSF (%) | |
|---|---|---|
| | Supernatant | Precipitate |
| 20 | 0.3 | 99.7 |
| 10 | 66.1 | 33.9 |
| 5 | 79.2 | 20.8 |
| 2 | 89.0 | 11.0 |

As shown in Table 2, when a zinc acetate solution having a final concentration of 20 mM was used (G-CSF:Zn(w/w)=1:1.3), not less than 99% of G-CSF was contained in the precipitate, whereas when the final concentration was not more than 10 mM, the precipitation rate of G-CSF was dramatically decreased.

Example 3

Studies of Zinc Concentration Required for Making Precipitate at 99% or More from 1 mg/ml of G-CSF Solution without Phosphate (1) A preparation in which final concentration of zinc is 20 mM was prepared by first mixing 80 μl of G-CSF solution (2.5 mg/ml) dissolved in injectable water, 8 μl of sodium hydrogen carbonate (0.5 M) and 104 μl of Milli-Q water, then adding to this solution 8 μl of zinc acetate solution (0.5 M) under stirring, and leaving the resultant solution at room temperature for 10 minutes.

(2) A preparation in which final concentration of zinc is 15 mM was prepared by first mixing 80 μl of G-CSF solution (2.5 mg/ml) dissolved in injectable water, 6 μl of sodium hydrogen carbonate (0.5 M) and 108 μl of Milli-Q water, then adding to this solution 6 μl of zinc acetate solution (0.5 M) under stirring, and leaving the resultant solution at room temperature for 10 minutes.

(3) A preparation in which final concentration of zinc is 10 mM was prepared by first mixing 80 μl of G-CSF solution (2.5 mg/ml) dissolved in injectable water, 4 μl of sodium hydrogen carbonate (0.5 M) and 112 μl of Milli-Q water, then adding to this solution 4 μl of zinc acetate solution (0.5 M) under stirring, and leaving the resultant solution at room temperature for 10 minutes.

(4) A preparation in which final concentration of zinc is 5 mM was prepared by first mixing 80 μl of G-CSF solution (2.5 mg/ml) dissolved in injectable water, 2 μl of sodium hydrogen carbonate (0.5 M) and 116 μl of Milli-Q water, then adding to this solution 2 μl of zinc acetate solution (0.5 M) under stirring, and leaving the resultant solution at room temperature for 10 minutes.

These suspensions (1) to (4) were centrifuged at approximately 10,000×g. The supernatants were collected and the precipitates were dissolved in 0.1 M EDTA solution (pH 7.4), and the amounts of G-CSF contained in the supernatants and precipitates were determined by ELISA method. The results are shown in Table 3.

TABLE 3

Zinc concentration and G-CSF content of precipitates formed by using zinc acetate and sodium hydrogen carbonate from the solution of 1 mg/ml G-CSF concentration

| Concentration of zinc acetate and sodium hydrogen carbonate (mM) | Content of G-CSF (%) | |
|---|---|---|
| | Supernatant | Precipitate |
| 20 | 0.7 | 99.3 |
| 15 | 0.7 | 99.3 |
| 10 | 1.3 | 98.7 |
| 5 | 0.7 | 99.3 |

As is apparent from the results shown in Table 3, when a phosphate was not presented in formation of precipitate, even a zinc acetate solution with final concentration of as low as 5 mM (G-CSF:Zn (w/w)=1:0.33) could make about 99% of G-CSF precipitate.

Example 4

Effect of Phosphate on Precipitate Formation of G-CSF from 1 mg/ml of G-CSF Solution by Using 20 mM Zinc Acetate and 20 mM Sodium Hydrogen Carbonate Mixture of 80 µl of desalted G-CSF solution (2.5 mg/ml) (final concentration: 1 mg/ml) and 8 µl sodium hydrogen carbonate (0.5 M) (final concentration: 20 mM) was first mixed with different proportions of phosphate buffer (0.2 M) (pH 7.2)/Milli-Q water as follow:

(1) 40 µl/64 µl (final phosphate concentration: 40 mM)
(2) 20 µl/84 µl (final phosphate concentration: 20 mM)
(3) 10 µl/94 µl (final phosphate concentration: 10 mM)
(4) 5 µl/99 µl (final phosphate concentration: 5 mM)
(5) 0 µl/104 µl (final phosphate concentration: 0 mM)

Then to these solutions was added 8 µl of zinc acetate solution (0.5 M) under stirring and left at room temperature for 10 minutes, to prepare suspensions having the respective final phosphate concentrations. These suspensions were centrifuged at approximately 10,000×g. The supernatants were collected and the precipitates were dissolved in 0.1 M EDTA solution (pH 7.4), and the amounts of G-CSF contained in the supernatants and precipitates were determined by ELISA method.

The results are shown in Table 4. As is apparent from the results shown in Table 4, when a precipitate of 1 mg/ml G-CSF was formed by the combination of 20 mM zinc acetate/20 mM sodium hydrogen carbonate, a phosphate did not inhibit formation of precipitate of G-CSF at a final concentration of 10 mM or less.

TABLE 4

G-CSF content of precipitates formed by using 20 mM zinc acetate and 20 mM sodium hydrogen carbonate from the solution of 1 mg/ml G-CSF concentration with phosphate

| Concentration of phosphate (mM) | Content of G-CSF (%) | |
|---|---|---|
| | Supernatant | Precipitate |
| 40 | 73.3 | 26.7 |
| 20 | 50.1 | 49.9 |
| 10 | 0.2 | 99.8 |
| 5 | 0.2 | 99.8 |
| 0 | 0.1 | 99.9 |

Example 5

Blood Kinetic Profile of G-CSF Sustained-Release Preparation Prepared by Using G-CSF Dissolved in Phosphate Buffer (1) A sustained-release preparation containing 2 mg/ml of G-CSF was prepared by first mixing 1000 µl of G-CSF solution (4.0 mg/ml) dissolved in approximately 30 mM phosphate buffer, 160 µl of sodium hydrogen carbonate (0.5 M) and 680 µl of Milli-Q water, and adding to this solution 160 µl of zinc acetate solution (0.5 M) under stirring.

(2) A sustained-release preparation containing 0.2 mg/ml of G-CSF was prepared by first mixing 100 µl of G-CSF solution (4.0 mg/ml) dissolved in approximately 30 mM phosphate buffer, 160 µl of sodium hydrogen carbonate (0.5 M) and 1580 µl of Milli-Q water, and adding to this solution 160 µl of zinc acetate solution (0.5 M) under stirring.

(3) A sustained-release preparation containing 0.02 mg/ml of G-CSF was prepared by first mixing 10 µl of G-CSF solution (4.0 mg/ml) dissolved in approximately 30 mM phosphate buffer, 160 µl of sodium hydrogen carbonate (0.5 M) and 1670 µl of Milli-Q water, and adding to this solution 160 µl of zinc acetate solution (0.5 M) under stirring.

(4) A solution preparation containing 0.2 mg/ml of G-CSF was prepared by mixing 100 µl of G-CSF solution (4.0 mg/ml) dissolved in approximately 30 mM phosphate buffer and 1900 µl of Milli-Q water.

To these solutions (1) to (4) was added 0.1 g of mannitol, and each 5 ml/kg of the resultant solutions were administered subcutaneously to 8-week old ddY mice (2 mice per group). Blood sample (65 µl) was collected at 4 hours, 1, 2, 3 and 4 days after administration for measuring G-CSF concentration by ELISA method.

As is apparent from the results shown in Table 5, the sustained-release preparation containing G-CSF that was subcutaneously administered was observed in blood for several days in a sustained manner. In contrast to this, when the solution preparation was administered, G-CSF was detected in blood only for a day.

TABLE 5

Blood kinetic profile of G-CSF in mice administered with G-CSF preparation

| Preparation (Dosage) | Blood G-CSF concentration (ng/ml) | | | | |
|---|---|---|---|---|---|
| | 4 hrs. | 1 day | 2 days | 3 days | 4 days |
| Sustained-release preparation (2 mg/ml) | 907.35 | 272.44 | 77.62 | 15.74 | 0.30 |
| Sustained-release preparation (0.2 mg/ml) | 27.31 | 46.04 | 6.91 | 1.04 | 0.09 |
| Sustained-release preparation (0.02 mg/ml) | 1.13 | 0.84 | 0.06 | ND | ND |
| Solution preparation (0.2 mg/ml) | 208.02 | 0.24 | ND | ND | ND |

ND: Not detected

Example 6

Comparison of Blood Kinetic Profile Between G-CSF Sustained-Release Preparation Prepared Using G-CSF Dissolved in Phosphate Buffer, and G-CSF Sustained-Release Preparation Prepared Using G-CSF Solution without Phosphate by Desalting A sustained-release preparation containing phosphate was prepared by first mixing 250 µl of G-CSF solution (4.0 mg/ml) dissolved in approximately 30 mM phosphate buffer, 40 µl of sodium hydrogen carbonate (0.5 M) and 170 µl of Milli-Q water, and adding to this solution 40 µl of zinc acetate solution (0.5 M) under stirring. A sustained-release preparation without phosphate was prepared by first mixing 400 µl of desalted G-CSF solution (2.5 mg/ml), 40 µl of sodium hydrogen carbonate (0.5 M) and 20 μl of Milli-Q water in injectable water, and adding to this solution 40 μl of zinc acetate solution (0.5 M) under stirring. To these preparations was added 0.025 g of mannitol, and each 5 ml/kg of the resultant preparations were administered subcutaneously to 8-week old ddY mice (2 mice per group). Blood sample (65 μl) was collected at 4 hours, 1, 2, 3 and 4 days after administration for measuring G-CSF concentration by ELISA method.

As can be seen from the results in Table 6, the blood G-CSF concentration was retained about 10 holds by the G-CSF preparation containing phosphate.

TABLE 6

Blood kinetic profile of G-CSF in mice administered with G-CSF preparation

| Preparation | Blood G-CSF concentration (ng/ml) | | | | |
|---|---|---|---|---|---|
| | 4 hrs. | 1 day | 2 days | 3 days | 4 days |
| Sustained-release preparation (with phosphate) | 8457.41 | 747.93 | 59.41 | 9.03 | 1.94 |
| Sustained-release preparation (without phosphate) | 1891.14 | 590.43 | 12.18 | 0.78 | 0.24 |

Example 7

Influence of Quantitative Ratio Between G-CSF and Zinc on Sustained Releasability in G-CSF Sustained-Release Preparation (1) A preparation in which molar ratio of G-CSF:Zn is 1:400 was prepared by first mixing 834 μl of desalted G-CSF solution (2.4 mg/ml), 80 μl of sodium hydrogen carbonate (0.5 M) and 6 μl of Milli-Q water, and then adding to this solution 80 μl of zinc acetate solution (0.5 M) under stirring.
(2) A preparation in which molar ratio of G-CSF:Zn is 1:200 was prepared by first mixing 834 μl of desalted G-CSF solution (2.4 mg/ml), 40 μl of sodium hydrogen carbonate (0.5 M) and 86 μl of Milli-Q water, and then adding to this solution 40 μl of zinc acetate solution (0.5 M) under stirring.
(3) A preparation in which molar ratio of G-CSF:Zn is 1:100 was prepared by first mixing 834 μl of desalted G-CSF solution (2.4 mg/ml), 20 μl of sodium hydrogen carbonate (0.5 M) and 126 μl of Milli-Q water, and then adding to this solution 20 μl of zinc acetate solution (0.5 M) under stirring.
(4) A preparation (not containing carbonate) in which molar ratio of G-CSF:Zn is 1:400 was prepared by first mixing 834 μl of desalted G-CSF solution (2.4 mg/ml) and 86 μl of Milli-Q water, and then adding to this solution 80 μl of zinc acetate solution (0.5 M) under stirring.

To these preparations was added 0.05 g of mannitol, and each 5 ml/kg of the resultant preparations were administered subcutaneously to 8-week old ddY mice (2 mice per group). Blood sample (65 μl) was collected at 4 hours, 1, 2, 3 and 4 days after administration for measuring G-CSF concentration by ELISA method.

The results are shown in Table 7. As is apparent from the results in Table, the sustained releasability of preparation gets worse in accordance with the smaller ratio of zinc to G-CSF. At the same ratio of zinc to G-CSF, the sustained releasability of the preparation not containing carbonate was significantly impaired.

TABLE 7

Blood kinetic profile of G-CSF in mice administered with G-CSF preparations with varying ratios of G-CSF to zinc

| G-CSF preparation | Blood G-CSF concentration (ng/ml) | | | | |
|---|---|---|---|---|---|
| G-CSF:Zn ratio | 4 hrs. | 1 day | 2 days | 3 days | 4 days |
| 1:400 | 1772.29 | 449.93 | 26.35 | 0.59 | 0.23 |
| 1:200 | 5811.21 | 214.2 | 0.94 | 0.09 | ND |
| 1:100 | 5187.81 | 87.72 | 0.27 | ND | ND |
| (without carbonate) | 1463.42 | 191.69 | 1.71 | 0.06 | ND |

ND: Not detected

Example 8

Sustained Releasability Control of Zinc-Containing G-CSF Sustained-Release Preparation by Carbonate and Phosphate (1) A preparation using carbonate was prepared by first mixing 640 μl of desalted G-CSF solution (2.3 mg/ml) and 64 μl of sodium hydrogen carbonate (0.5 M), and adding to this solution 64 μl of zinc acetate solution (0.5 M) under stirring.
(2) A preparation using both carbonate and phosphate was prepared by first mixing 640 μl of desalted G-CSF solution (2.3 mg/ml), 64 μl of sodium hydrogen carbonate (0.5 M) and 40 μl of phosphate buffer (0.2 M) at pH 7.2, and then adding to this solution 64 μl of zinc acetate solution (0.5 M) under stirring.
(3) A preparation using phosphate was prepared by first mixing 640 μl of desalted G-CSF solution (2.3 mg/ml) and 20 μl of phosphate buffer (0.2 M) at pH 7.2, and then adding to this solution 64 μl of zinc acetate solution (0.5 M) under stirring.

To these preparations was added 0.04 g of mannitol, and each 5 ml/kg of the resultant preparations were administered subcutaneously to 8-week old ddY mice (2 mice per group). Blood sample (65 μl) was collected at 4 hours, 1, 2, 3 and 4 days after administration for measuring G-CSF concentration by ELISA method.

The results are shown in Table 8. As can be seen from the results in Table 8, addition of carbonate or phosphate in production of zinc-containing G-CSF preparation resulted in difference in sustained releasability, and excellent sustained releasability was achieved when both carbonate and phosphate were used. It was also found that the sustained-release rate can be controlled by changing the mixing ratio of carbonate and phosphate.

TABLE 8

Blood kinetic profile of G-CSF in mice administered with zinc-containing G-CSF sustained release preparations using carbonate and/or phosphate

| Preparation | Blood G-CSF concentration (ng/ml) | | | | |
|---|---|---|---|---|---|
| | 4 hrs. | 1 day | 2 days | 3 days | 4 days |
| Zinc acetate/ Sodium hydrogen carbonate | 3335.96 | 692.46 | 25.92 | 0.59 | 0.15 |

TABLE 8-continued

Blood kinetic profile of G-CSF in mice administered with zinc-containing G-CSF sustained release preparations using carbonate and/or phosphate

| Preparation | Blood G-CSF concentration (ng/ml) | | | | |
|---|---|---|---|---|---|
| | 4 hrs. | 1 day | 2 days | 3 days | 4 days |
| Zinc acetate/ Sodium hydrogen carbonate/ Phosphate buffer | 4683.65 | 742.90 | 50.72 | 3.90 | 0.67 |
| Zinc acetate/ Phosphate buffer | 11104.73 | 75.64 | 1.55 | 0.43 | 0.18 |

Example 9

Influence by Freeze-Drying of G-CSF Sustained-Release Preparation and its Blood Kinetic Profile First mixing 0.5 ml of G-CSF solution (4.0 mg/ml) dissolved in approximately 30 mM phosphate buffer, 4.0 ml of sodium hydrogen carbonate (0.1 M) and 4.7 ml of Milli-Q water, this solution was added with 0.8 ml of zinc acetate solution (0.5 M) under stirring to form a precipitate, then added with 0.5 g of mannitol or trehalose, dispensed into 1 ml aliquots and freeze-dried. To 450 µl of sample before freeze-drying was added 50 µl of 0.5 M EDTA to dissolve the precipitate, from which a 100 µl portion was analyzed by reverse-phase HPLC. The sample after freeze-drying was re-suspended in 1 ml of injectable water, from which 450 µl was drawn out and the precipitate was dissolved by adding 50 µl of 0.5 M EDTA. A 100 µl portion was analyzed by reverse-phase HPLC in the similar manner as described above. Recovery of G-CSF was compared based on the area of elution peak.

The results are shown in Table 9. As is apparent from the results in Table, G-CSF was recovered at almost 100% even after freeze-drying, and neither aggregation nor decomposition was observed.

TABLE 9

Recovery of G-CSF after freeze-drying G-CSF sustained-release preparation

| | Mannitol | | Trehalose | |
|---|---|---|---|---|
| | Peak area of G-CSF (mAU × ml) | Recovery (%) | Peak area of G-CSF (mAU × ml) | Recovery (%) |
| Before freeze-drying | 357.0643 | 100 | 346.3886 | 100 |
| After freeze-drying | 373.9416 | 105 | 333.5237 | 96 |

Since the availability of freeze-drying was confirmed, the experiment of Example 5 was carried out using freeze-dried preparations. Freeze-dried preparations were re-suspended in 0.5% carmellose, and each 5 ml/kg of these solutions was administered subcutaneously by single dose to 8-week old ddY mice. Sustained release effect was observed also in the freeze-dried preparations as shown in Table 10.

TABLE 10

Blood kinetic profile of G-CSF in mice administered with freeze-dried G-CSF sustained-release preparation

| Preparation (dosage) | Blood G-CSF concentration (ng/ml) | | | | |
|---|---|---|---|---|---|
| | 4 hrs. | 1 day | 2 days | 3 days | 4 days |
| Sustained-release preparation (2 mg/ml) | 4683.35 | 497.86 | 49.89 | 6.86 | 1.66 |
| Sustained-release preparation (0.2 mg/ml) | 46.30 | 49.11 | 8.42 | 0.94 | 0.41 |
| Sustained-release preparation (0.02 mg/ml) | 0.33 | 0.57 | 0.12 | 0.06 | 0.06 |
| Solution preparation (0.2 mg/ml) | 283.90 | 0.62 | ND | ND | ND |

ND: Not detected

Example 10

Effect of Adding Mannitol on Sustained Releasability in G-CSF Sustained-Release Preparation A sustained-release preparation containing mannitol was prepared by first mixing 476 µl of G-CSF solution (4.2 mg/ml) dissolved in approximately 30 mM phosphate buffer, 80 µl of sodium hydrogen carbonate (0.5 M) and 364 µl of Milli-Q water, then adding to this solution 80 µl of zinc acetate solution (0.5 M) under stirring, and adding 0.05 g of mannitol.

A sustained-release preparation not containing mannitol was prepared by first mixing 476 µl of G-CSF solution (4.2 mg/ml) dissolved in approximately 30 mM phosphate buffer, 80 µl of sodium hydrogen carbonate (0.5 M) and 364 µl of saline, and adding to this solution 80 µl of zinc acetate solution (0.5 M).

Each 5 ml/kg of these preparations was administered subcutaneously to 8-week old ddY mice (2 mice per group). Blood sample (65 µl) was collected at 4 hours, 1, 2, 3 and 4 days after administration for measuring G-CSF concentration by ELISA method.

The results are shown in Table 11. As shown in Table 11, addition of mannitol did not show any effect of improving the sustained releasability.

TABLE 11

Blood kinetic profile of G-CSF in mice administered with G-CSF preparation

| Preparation | Blood G-CSF concentration (ng/ml) | | | | |
|---|---|---|---|---|---|
| | 4 hrs. | 1 day | 2 days | 3 days | 4 days |
| Sustained-release preparation (with mannitol) | 4193.76 | 290.37 | 62.95 | 7.96 | 2.95 |
| Sustained-release preparation (without mannitol) | 3700.81 | 803.20 | 67.07 | 16.08 | 6.92 |

Example 11

Leukocyte Increasing Effect of G-CSF Sustained-Release Preparation

To each of a sustained-release preparation containing 0.2 mg/ml of G-CSF which was prepared by first mixing 100 μl of G-CSF solution (4.0 mg/ml) dissolved in approximately 30 mM phosphate buffer, 160 μl of sodium hydrogen carbonate (0.5 M) and 1580 μl of Milli-Q water, and adding to this solution 160 μl of zinc acetate solution (0.5 M) under stirring; and a sustained-release preparation containing 0.02 mg/ml of G-CSF which was prepared by first mixing 10 μl of G-CSF solution (4.0 mg/ml) dissolved in approximately 30 mM phosphate buffer, 160 μl of sodium hydrogen carbonate (0.5 M) and 1670 μl of Milli-Q water, and adding to this solution 160 μl of zinc acetate solution (0.5 M) under stirring, 0.1 g of mannitol was added and the mixture was freeze-dried. The resultant freeze-dried preparations were re-suspended by adding 0.5% carmellose, and each 5 ml/kg of preparations was subcutaneously administered to 7-week old ddY mice (3 mice per group) by single dose. Blood sample (35 μl) was collected for 12 days, and the number of leucocytes was counted by using an automatic blood cell counter.

The results are shown in Table 12. As shown in Table 12, although there is a difference in increased number of leukocyte depending on the dosage, the drug efficacy was retained over a week for both dosages.

TABLE 12

Change in number of leukocytes in mice administered with G-CSF sustained-release preparation

| | Number of leukocytes (× $10^2$ cells/mm$^3$) Dosage amount | |
|---|---|---|
| | 0.2 mg/ml G-CSF | 0.02 mg/ml G-CSF |
| Before administration | 75 ± 15 | 81 ± 30 |
| Day 1 | 156 ± 30 | 189 ± 60 |
| Day 2 | 326 ± 53 | 294 ± 92 |
| Day 3 | 383 ± 103 | 275 ± 85 |
| Day 4 | 359 ± 36 | 240 ± 93 |
| Day 5 | 416 ± 57 | 239 ± 102 |
| Day 6 | 342 ± 184 | 173 ± 55 |
| Day 8 | 264 ± 151 | 106 ± 29 |
| Day 9 | 171 ± 107 | 94 ± 9 |
| Day 10 | 188 ± 109 | 83 ± 9 |
| Day 11 | 132 ± 75 | 72 ± 17 |
| Day 12 | 114 ± 20 | 96 ± 29 |

Example 12

Comparison of Leukocyte Increasing Effect Between G-CSF Sustained-Release Preparation and G-CSF Solution Preparation (1) A sustained-release preparation containing 0.1 mg/ml of G-CSF was prepared by first mixing 28.6 μl of G-CSF solution (4.2 mg/ml) dissolved in approximately 30 mM phosphate buffer, 48 μl of sodium hydrogen carbonate (0.5 M) and 1075.4 μl of Milli-Q water, then adding to this solution 48 μl of zinc acetate solution (0.5 M) under stirring to form a precipitate, and adding 0.06 g of mannitol.

(2) A solution preparation containing 0.1 mg/ml of G-CSF was prepared by first mixing 48 μl of G-CSF solution (4.2 mg/ml) dissolved in approximately 30 mM phosphate buffer and 1952 μl of Milli-Q water, and then adding 0.1 g of mannitol.

The preparations prepared as described above were freeze-dried. The resultant freeze-dried preparations were re-suspended by adding 0.5% carmellose, and each 10 ml/kg preparations were administered by single dose to 7-week old ddY mice (3 mice per group).

For everyday administration, 38.4 μl of G-CSF solution (4.2 mg/ml) dissolved in approximately 30 mM phosphate buffer and 7961.6 μl of Milli-Q water were mixed and then 0.4 g of mannitol was added to prepare a 0.02 mg/ml solution preparation, which was then dispensed into 1.5 ml aliquots and freeze-dried to prepare a freeze-dried preparation containing G-CSF. Each 10 ml/kg of preparations were administered to 7-week old ddY mice (three animals) everyday for initial five days.

In each test, blood sample (35 μl) was collected for 12 days, and the number of leukocytes was counted by using an automatic blood cell counter.

The results are shown in Table 13. As shown in Table 13, the solution preparation administered in an equivalent amount of the sustained-release preparation by single dose retained its drug efficacy for only about two days. The sustained-release preparation administered by single dose showed comparable or better drug efficacy than that achieved by the solution preparation administered by five everyday doses. While the solution preparation lost its drug efficacy immediately after end of administration, the sustained-release preparation showed retention of drug efficacy.

TABLE 13

Comparison of leukocyte number increasing effect between mice administered with G-CSF sustained-release preparation (single dose) and mice administered with solution preparation (single dose and five everyday doses)

| | Number of leukocytes (× $10^2$ cells/mm$^3$) | | |
|---|---|---|---|
| Preparation | Sustained-release preparation | Solution preparation | Solution preparation |
| G-CSF dosage | 0.1 mg/ml | 0.1 mg/ml | 0.02 mg/ml |
| Number of doses | Single dose | Single dose | 5 days dose |
| Before administration | 76 ± 18 | 87 ± 7 | 64 ± 31 |
| Day 1 | 141 ± 28 | 162 ± 31 | 147 ± 35 |
| Day 2 | 302 ± 81 | 161 ± 21 | 267 ± 69 |
| Day 3 | 294 ± 110 | 96 ± 15 | 312 ± 51 |
| Day 4 | 262 ± 76 | 92 ± 16 | 303 ± 58 |
| Day 5 | 342 ± 124 | 89 ± 33 | 392 ± 108 |
| Day 6 | 280 ± 128 | 93 ± 26 | 80 ± 12 |
| Day 8 | 156 ± 37 | 92 ± 35 | 79 ± 28 |
| Day 9 | 112 ± 34 | 90 ± 28 | 72 ± 30 |
| Day 10 | 115 ± 28 | 102 ± 34 | 76 ± 19 |
| Day 11 | 93 ± 27 | 76 ± 23 | 71 ± 25 |
| Day 12 | 82 ± 28 | 73 ± 26 | 67 ± 20 |

Example 13

Comparison of Leukocyte Number Increasing Effect of G-CSF Sustained-Release Preparation Produced by Using Zinc Acetate or Zinc Chloride To a sustained-release preparation containing 0.1 mg/ml of G-CSF which was prepared by first mixing 50 μl of G-CSF solution (4.0 mg/ml) dissolved in approximately 30 mM phosphate buffer, 80 μl of sodium hydrogen carbonate (0.5 M) and 1790 μl of Milli-Q water, and adding to this solution 80 µl of zinc acetate solution (0.5 M) or 80 µl of zinc chloride (0.5 M) under stirring, 0.1 g of mannitol was added and the mixture was freeze-dried. The resultant freeze-dried preparation was resuspended by adding 0.5% carmellose, each 10 ml/kg of these preparations was administered to 7-week old ddY mice (3 mice per group) by single dose, blood (35 µl) was collected for 12 days, and the number of leukocytes was counted by an automatic blood cell counter.

The results are shown in Table 14. As shown in Table 14, both of the sustained-release preparations prepared by using respectively zinc acetate and zinc chloride in production of sustained-release preparation exhibited similar drug efficacies.

TABLE 14

Change in number of leukocytes in mice administered with G-CSF sustained-release preparation

| Sustained-release preparation | Number of leukocytes ($\times 10^2$ cells/mm$^3$) | |
|---|---|---|
| | Using zinc acetate | Using zinc chloride |
| Before administration | 70 ± 12 | 71 ± 9 |
| Day 1 | 168 ± 32 | 147 ± 21 |
| Day 2 | 352 ± 71 | 272 ± 32 |
| Day 3 | 340 ± 89 | 271 ± 22 |
| Day 4 | 362 ± 101 | 293 ± 23 |
| Day 5 | 468 ± 72 | 423 ± 25 |
| Day 6 | 502 ± 93 | 429 ± 118 |
| Day 8 | 426 ± 98 | 363 ± 118 |
| Day 9 | 361 ± 39 | 306 ± 151 |
| Day 10 | 324 ± 36 | 275 ± 157 |
| Day 11 | 268 ± 50 | 202 ± 146 |
| Day 12 | 188 ± 113 | 143 ± 57 |

Example 14

Effect of Increasing and Maintaining Leukocytes by G-CSF Sustained-Release Preparation Containing Chondroitin Sulfate A sustained-release preparation containing 0.1 mg/ml of G-CSF was prepared by first mixing 28.6 µl of G-CSF solution (4.2 mg/ml) dissolved in approximately 30 mM phosphate buffer, 48 µl of sodium hydrogen carbonate (0.5 M) and 1075.4 µl of Milli-Q water, and then adding to this solution 48 µl of zinc acetate solution (0.5 M) under stirring; and a 0.1 mg/ml G-CSF preparation containing chondroitin sulfate was prepared by first mixing 28.6 µl of G-CSF solution (4.2 mg/ml) dissolved in approximately 30 mM phosphate buffer, 48 µl of sodium hydrogen carbonate (0.5 M) and 1015.4 µl of Milli-Q water, and then adding to this solution 48 µl of zinc acetate solution (0.5 M) under stirring, followed by 60 µl of chondroitin sulfate (20 mg/ml).

To these preparations was added 0.06 g of mannitol and then they were freeze-dried. The resultant freeze-dried preparation was re-suspended by adding 0.5% carmellose, each 10 ml/kg of these preparations was administered to 7-week old ddY mice (3 mice per group) by single dose, blood sample (35 µl) was collected for 12 days, and the number of leukocytes was counted by using an automatic blood cell counter.

The results are shown in Table 15. As shown in Table 15, while the maximum value of the number of leukocytes decreased in the preparation added with chondroitin sulfate, continuous increase in number of leukocytes was observed more clearly.

TABLE 15

Change in number of leukocytes in mice administered with G-CSF sustained-release preparation

| Sustained-release preparation | Number of leukocytes ($\times 10^2$ cells/mm$^3$) | |
|---|---|---|
| | Without chondroitin sulfate | With chondroitin sulfate |
| Before administration | 84 ± 19 | 80 ± 7 |
| Day 1 | 138 ± 37 | 159 ± 28 |
| Day 2 | 307 ± 101 | 237 ± 49 |
| Day 3 | 293 ± 114 | 183 ± 36 |
| Day 4 | 255 ± 79 | 175 ± 44 |
| Day 5 | 313 ± 98 | 226 ± 33 |
| Day 6 | 218 ± 29 | 197 ± 8 |
| Day 8 | 145 ± 42 | 145 ± 22 |
| Day 9 | 97 ± 6 | 128 ± 26 |
| Day 10 | 115 ± 36 | 132 ± 11 |
| Day 11 | 100 ± 25 | 135 ± 34 |
| Day 12 | 77 ± 37 | 124 ± 30 |

Example 15

Leukocyte Increasing Effect of G-CSF Sustained-Release Preparation Using Phosphate A sustained-release preparation containing 0.1 mg/ml of G-CSF was prepared by first mixing 100 µl of G-CSF solution (4.0 mg/ml) dissolved in approximately 30 mM phosphate buffer, 400 µl of sodium phosphate buffer (0.2 M) at pH 7.2 and 3340 µl of Milli-Q water, and adding 160 µl of zinc acetate solution (0.5 M) under stirring. This preparation was added with 0.1 g of mannitol and freeze-dried. The resultant freeze-dried preparation was re-suspended by adding injectable water, and 10 ml/kg of the preparation was administered to each of 7-week old ddY mice (3 mice per group) by single dose, blood (35 µl) was collected for 12 days, and the number of leukocytes was counted by an automatic blood cell counter.

The results are shown in Table 16. As shown in Table, the drug efficacy was retained over a week even in the zinc-containing sustained-release preparation using phosphate rather than carbonate.

TABLE 16

Change in number of leukocytes in mice administered with G-CSF sustained-release preparation

| Sustained-release preparation | Number of leukocytes ($\times 10^2$ cells/mm$^3$) 0.1 mg/ml G-CSF |
|---|---|
| Before administration | 82 ± 9 |
| Day 1 | 175 ± 18 |
| Day 2 | 258 ± 17 |
| Day 3 | 246 ± 60 |
| Day 4 | 207 ± 40 |
| Day 5 | 262 ± 60 |
| Day 6 | 237 ± 15 |
| Day 8 | 166 ± 21 |
| Day 9 | 142 ± 23 |
| Day 10 | 139 ± 16 |
| Day 11 | 106 ± 16 |
| Day 12 | 126 ± 16 |

Example 16

G-CSF Content in Precipitate Prepared by Lastly Adding G-CSF and Drug Efficacy of Precipitate Preparation First mixing 16 µl of sodium hydrogen carbonate solution (0.5 M) and 158 µl of Milli-Q water, which solution was then added with 16 µl of zinc acetate solution (0.5 M) under stirring and further with 10 µl of G-CSF solution (4.0 mg/ml) dissolved in approximately 30 mM phosphate buffer under stirring, and left for 10 minutes at room temperature. The suspension was centrifuged at approximately 10,000×g, the supernatant collected, and the resultant precipitate was dissolved in 0.1 M EDTA solution (pH 7.4). The contents of G-CSF contained in the supernatant and precipitate were determined by ELISA method. As a result, almost 100% of G-CSF was contained in the precipitate.

In order to examine the drug efficacy, first mixing 176 µl of an aqueous solution of sodium hydrogen carbonate (0.5 M) and 1738 µl of Milli-Q water, which solution was then added with 176 µl of zinc acetate solution (0.5 M) under stirring and further with 110 µl of G-CSF solution (4.0 mg/ml) dissolved in approximately 30 mM phosphate buffer under stirring, to thereby prepare a sustained-release preparation containing 0.2 mg/ml of G-CSF. The resultant preparation was added with 0.11 g of mannitol and freeze-dried. The resultant freeze-dried preparation was re-suspended by adding injectable water, and 5 ml/kg of the preparation was administered to each of 7-week old ddY mice (3 mice per group) by single dose, blood sample (35 µl) was collected for 12 days, and the number of leukocytes was counted by using an automatic blood cell counter.

The results are shown in Table 17. As shown in Table 17, sufficient retention of drug efficacy was confirmed even in the precipitate preparation prepared by first adding zinc acetate and an aqueous solution of sodium hydrogen carbonate, and then adding G-CSF.

TABLE 17

Change in number or leukocytes in mice administered with G-CSF sustained-release preparation

| Sustained-release preparation | Number of leukocytes ($\times 10^2$ cells/mm$^3$) 0.2 mg/ml G-CSF |
|---|---|
| Before administration | 51 ± 9 |
| Day 1 | 100 ± 35 |
| Day 2 | 277 ± 94 |
| Day 3 | 242 ± 119 |
| Day 4 | 185 ± 54 |
| Day 5 | 299 ± 76 |
| Day 6 | 285 ± 115 |
| Day 8 | 271 ± 103 |
| Day 9 | 221 ± 105 |
| Day 10 | 167 ± 86 |
| Day 11 | 125 ± 51 |
| Day 12 | 124 ± 39 |

Example 17

Precipitation Rate in Precipitate Formation by Mixing of Zinc Acetate Solution (20 mM) and Sodium Hydrogen Carbonate Solution (20 mM), with Regard to Anti-TNF Antibody (monoclonal), Interferon-α and Growth Hormone First 10 µl of anti-TNF antibody solution (10 mg/ml), 8 µl of sodium hydrogen carbonate solution (0.5 M) and 174 µl of Milli-Q water were mixed, and the resultant solution was then added with 8 µl of zinc acetate solution (0.5 M) under stirring, and left for 10 minutes at room temperature, to thereby obtain a suspension.

In the similar manner, first 77 µl of interferon-α (1.3 mg/ml), 8 µl of sodium hydrogen carbonate aqueous solution (0.5 M) and 107 µl of Milli-Q water were mixed, and the resultant solution was then added with 8 µl zinc acetate solution (0.5 M) under stirring, and left for 10 minutes at room temperature, to thereby obtain a suspension.

Furthermore, first 200 µl of growth hormone (0.5 mg/ml), 16 µl of sodium hydrogen carbonate solution (0.5 M) and 168 µl or Milli-Q water were mixed, and the resultant solution was then added with 16 µl of zinc acetate solution (0.5 M) under stirring and left for 10 minutes at room temperature, to thereby obtain a suspension.

Each of these suspensions was centrifuged at approximately 10,000×g, supernatant collected, and the precipitate was dissolved in 0.1 M EDTA solution (ph 7.4). Anti-TNT antibody and interferon-α contained in the supernatant and precipitate were quantified by ELISA method and growth hormone was quantified by reverse-phase HPLC.

The results are shown in Table 18. As shown in Table 18, proteins known to bind with zinc such as anti-TNF antibody, interferon-α and growth hormone resulted in very high content in precipitate comparable to that achieved by G-CSF when 0.5 mg/ml of anti-TNF antibody or interferon-α, or 0.25 mg/ml of growth hormone was mixed with the sodium hydrogen carbonate solution and zinc acetate solution for forming a precipitate.

TABLE 18

Content of anti-TNF antibody, interferon-α and growth hormone

| | Content of Protein (%) | |
|---|---|---|
| | Supernatant | Precipitate |
| Anti-TNF antibody | 0.1 | 99.9 |
| Interferon-α | 2.0 | 98.0 |
| Growth hormone | 0.8 | 99.2 |

Example 18

Control of Sustained Releasability in Zinc-Containing Human Growth Hormone (hGH) Sustained-Release Preparation by Carbonate and Phosphate (1) A preparation using carbonate was prepared by first mixing 720 µl of desalted hGH solution (0.5 mg/ml), 24 µl of sodium hydrogen carbonate solution (0.5 M) and 432 µl of Milli-Q water, and adding 24 µl of zinc acetate solution (0.5 M) under stirring.

(2) A preparation using both carbonate and phosphate was prepared by first mixing 720 µl of desalted hGH solution (0.5 mg/ml), 24 μl of sodium hydrogen carbonate solution (0.5 M), 30 μl of phosphate buffer (0.2 M) at pH 7.2 and 402 μl of Milli-Q water, and adding 24 μl of zinc acetate solution (0.5 M) under stirring.

(3) A solution preparation was prepared by mixing 720 μl of desalted hGH solution (0.5 mg/ml), 24 μl of sodium hydrogen carbonate solution (0.5 M) and 432 μl of Milli-Q water.

These preparations were added with 0.03 g of mannitol, and then freeze-dried. Prior to administration, the preparations (1) and (2) were dissolved in 600 μl of 20 mM zinc acetate/20 mM sodium hydrogen carbonate mixture, and the preparation (3) was dissolved in 600 μl of Milli-Q water. Each 5 ml/kg of the above preparations was administered subcutaneously to 7 week-old ddY mice (2 mice per group). At 4 hours, 1, 2, 3 and 4 days after administration, blood sample (65 μl) was collected, and hGH concentration was measured by an automatic EIA apparatus.

The results are shown in Table 19. As is apparent from the results in Table, the hGH preparation containing combination of zinc/carbonate eluted the drug in a sustained manner. By adding a phosphate to this preparation, the sustained releasability improves, so that elution after several hours is suppressed and higher blood concentration of hGH was observed for additional several days.

TABLE 19

Blood kinetics of hGH in mice administered with zinc-containing hGH sustained-release preparation

| Preparation | Blood hGH concentration (ng/ml) | | | | |
|---|---|---|---|---|---|
| | 4 hrs. | 1 day | 2 days | 3 days | 4 days |
| Zinc acetate/ Sodium hydrogen carbonate | 79.05 | 7.94 | 2.27 | 0.62 | 0.24 |
| Zinc acetate/ Sodium hydrogen carbonate/ Phosphate buffer | 9.15 | 17.00 | 5.22 | 3.03 | 1.56 |
| Sodium hydrogen carbonate | 92.88 | ND | ND | ND | ND |

ND: Not Detected

Example 19

Stability of Freeze-Dried G-CSF Sustained-Release Preparation

First 0.5 ml of G-CSF (4.0 mg/ml) dissolved in approximately 30 mM phosphate buffer, 0.8 ml of sodium hydrogen carbonate (0.5 M) and 7.9 ml of Milli-Q water were mixed, and 0.8 ml of zinc acetate solution (0.5 M) was added to the mixture under stirring to form a precipitate, after which 0.5 g of trehalose was added, charged into vials by 1 ml and then freeze-dried. After freeze-drying, the samples were placed in thermostatic chamber at 37° C. To 450 μl of sample before freeze-drying, 50 μl of 0.5 M EDTA was added to dissolve the precipitate. 100 μl of the resultant solution was subjected to reverse-phase HPLC to determine the content of G-CSF. On the other hand, each 1 ml of samples of immediately after freeze-drying, 1-week and 4-week after storage in thermostatic chamber was re-suspended in injectable water, from which 450 μl was drawn out. This was then added with 50 μl of 0.5 M EDTA to dissolve the precipitate, and 100 μl of the resultant solution was subjected to reverse-phase HPLC to determine G-CSF content.

On the basis of the area of elution peak of G-CSF, recovery of G-CSF was compared.

As shown in Table 20, almost 100% of G-CSF was recovered even when the freeze-dried G-CSF preparation was stored at 37° C. for four weeks, and aggregation and decomposition were not observed.

TABLE 20

4-week stability at 37° C. of freeze-dried G-CSF sustained-release preparation

| | Recovery of G-CSF (%) |
|---|---|
| Before freeze-drying | 100.0 |
| Immediately after freeze-drying | 88.1 |
| 1-week after freeze-drying | 90.0 |
| 4-week after freeze-drying | 90.6 |

Example 20

Preparation Example (Suspension Injection)

To a sustained-release preparation containing 0.2 mg/ml of G-CSF prepared in accordance with Example 10, mannitol was added and freeze-dried. The resultant freeze-dried preparation was charged into a vial, and by re-suspending the preparation by adding 0.5% carmellose or injectable water in other vial, a suspension injection was prepared.

INDUSTRIAL APPLICABILITY

As described above, the present invention provides a water-insoluble preparation which precipitates a physiologically active protein or peptide such as G-CSF with high yield and stabilizes the same, as well as enables the physiologically active protein or peptide to retain its drug efficacy for several days in a living body owing to the sustained releasability of the obtained precipitate. Therefore, the present invention makes significant contributions to the medical and pharmaceutical industry.

The invention claimed is:

1. A zinc-containing sustained-release composition consisting of a precipitate formed by mixing a physiologically active protein or peptide, a water-soluble zinc salt, an aqueous solution of a water-soluble carbonate, an aqueous solution of a water-soluble phosphate, and optionally non-polymer, pharmaceutically acceptable additives.

2. The zinc-containing sustained-release composition according to claim 1, wherein the water-soluble zinc salt is zinc acetate or zinc chloride.

3. A zinc-containing sustained-release composition consisting of a precipitate formed by mixing a physiologically active protein or peptide, a water-soluble zinc salt, an aqueous solution of a water-soluble carbonate, an aqueous solution of a water-soluble phosphate, and optionally non-polymer, pharmaceutically acceptable additives, wherein the molar ratio of the physiologically active protein or peptide and zinc in the water-soluble zinc salt is 1:100 or more.

4. A zinc-containing sustained-release composition consisting of a precipitate formed by mixing a physiologically active protein or peptide, a water-soluble zinc salt, an aqueous solution of a water-soluble carbonate, an aqueous solution of water-soluble phosphate, and optionally non-polymer, pharmaceutically acceptable additives, wherein the molar ratio of the physiologically active protein or peptide and zinc in the water-soluble zinc salt is 1:100 or more and wherein the water-soluble carbonate is sodium carbonate or sodium hydrogen carbonate.

5. A zinc-containing sustained-release composition consisting of a precipitate formed by mixing a physiologically active protein or peptide, a water-soluble zinc salt, an aqueous solution of a water-soluble carbonate, an aqueous solution of a water-soluble phosphate and optionally non-polymer, pharmaceutically acceptable additives, wherein the molar ratio of the physiologically active protein or peptide and zinc in the water-soluble zinc salt is 1:100 or more and wherein the water-soluble phosphate is sodium phosphate or sodium hydrogen phosphate.

6. The zinc-containing sustained-release composition according to claim 3, wherein the physiologically active protein is G-CSF, antibody, growth hormone, IFN, EPO, GM-CSF, BDNF, NT-3, TNF antibody, interleukin or FGF.

7. The zinc-containing sustained-release composition according to claim 3, wherein the zinc-containing sustained-release composition is freeze-dried.

8. The zinc-containing sustained-release composition according to claim 3, wherein the zinc-containing sustained-release composition is in a form suited for subcutaneous injection or intramuscular injection.

9. The zinc-containing sustained-release preparation according to claim 3, wherein the pharmaceutically acceptable additives are dispersants, surfactants, antiseptic agents and stabilizers.

10. The zinc-containing sustained-release preparation according to claim 3, wherein the pharmaceutically acceptable additives are saccharides.

11. The zinc-containing sustained-release preparation according to claim 3, wherein the zinc-containing sustained-release preparation is freeze-dried.

12. The zinc-containing sustained-release preparation according to claim 3, wherein the zinc-containing sustained-release preparation is in a form suited for subcutaneous injection or intramuscular injection.

13. A leukocyte-increasing agent comprising a zinc-containing sustained-release composition consisting of a precipitate formed by mixing G-CSF, a water-soluble zinc salt, an aqueous solution of a water-soluble carbonate, an aqueous solution of a water-soluble phosphate and optionally non-polymer, pharmaceutically acceptable additives.

14. A method for producing a zinc-containing sustained-release composition consisting of mixing a physiologically active protein or peptide, a water-soluble zinc salt, an aqueous solution of a water-soluble carbonate, an aqueous solution of a water-soluble phosphate and optionally non-polymer, pharmaceutically acceptable additives to form a precipitate.

\* \* \* \* \*

UNITED STATES PATENT AND TRADEMARK OFFICE
CERTIFICATE OF CORRECTION

PATENT NO. : 7,642,230 B2
APPLICATION NO. : 10/555191
DATED : January 5, 2010
INVENTOR(S) : Kimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this

Sixteenth Day of November, 2010

David J. Kappos
*Director of the United States Patent and Trademark Office*